(12) United States Patent
Yahav et al.

(10) Patent No.: US 10,188,484 B2
(45) Date of Patent: Jan. 29, 2019

(54) SYSTEM OF COMPONENTS OR IMPLEMENTS FOR EASILY AND PRECISELY INSTALLING A DENTAL IMPLANT, AND A METHOD OF INSTALLING THE DENTAL IMPLANT

(71) Applicants: Jonathon Yigal Yahav, Skokie, IL (US); Khasim Ali Khan, Bolingbrook, IL (US)

(72) Inventors: Jonathon Yigal Yahav, Skokie, IL (US); Khasim Ali Khan, Bolingbrook, IL (US)

( * ) Notice: Subject to any disclaimer, the term of this patent is extended or adjusted under 35 U.S.C. 154(b) by 0 days.

(21) Appl. No.: 15/354,024

(22) Filed: Nov. 17, 2016

(65) Prior Publication Data

US 2018/0132969 A1    May 17, 2018

(51) Int. Cl.
*A61C 1/08* (2006.01)
*A61C 8/00* (2006.01)

(52) U.S. Cl.
CPC ............ *A61C 1/084* (2013.01); *A61C 8/0089* (2013.01); *A61C 8/0027* (2013.01); *A61C 8/0037* (2013.01)

(58) Field of Classification Search
CPC .............................. A61C 1/084; A61C 8/0037
USPC ......................................................... 433/75
See application file for complete search history.

(56) References Cited

U.S. PATENT DOCUMENTS

| | | | |
|---|---|---|---|
| 3,600,810 A * | 8/1971 | Marshall | A61C 3/02 433/75 |
| 3,660,899 A | 5/1972 | Linkow | |
| 3,729,825 A | 5/1973 | Linkow et al. | |
| 3,798,771 A | 3/1974 | Edelman | |
| 3,829,972 A | 8/1974 | Pasqualini et al. | |
| 3,992,780 A * | 11/1976 | Herskovits | A61C 8/0089 433/176 |
| 4,179,810 A * | 12/1979 | Kirsch | A61B 17/1673 606/87 |
| 4,521,192 A | 6/1985 | Linkow | |
| 4,624,673 A * | 11/1986 | Meyer | A61C 8/005 433/173 |
| 4,802,847 A | 2/1989 | Komatsu | |
| 5,006,070 A | 4/1991 | Komatsu | |
| 5,032,129 A | 7/1991 | Kurze et al. | |
| 5,102,336 A | 4/1992 | Linkow | |

(Continued)

FOREIGN PATENT DOCUMENTS

| | | |
|---|---|---|
| EP | 0517529 | 12/1992 |
| FR | 2737847 | 2/1997 |

(Continued)

*Primary Examiner* — Matthew Nelson
(74) *Attorney, Agent, or Firm* — Law Offices Of Steven W. Weinrieb

(57) ABSTRACT

A system of components or implements for easily and precisely installing a dental implant, and a method of installing the dental implant, within a patient's jaw, is disclosed. The system comprises a rotary cutter guide and a rotary cutter. Orthogonal slots are defined within the rotary cutter guide so as to precisely position the rotary cutter within the rotary cutter guide as well as to permit the rotary cutter to form slots within a patient's jaw so as to accommodate winged members of a winged dental implant. A method of installation is also disclosed, and the system and method may be utilized in conjunction with the installation of both a single winged implant or a dual winged implant wherein the two winged implants are connected together by means of a connecting bar or plate.

17 Claims, 6 Drawing Sheets

(56) References Cited

U.S. PATENT DOCUMENTS

| | | |
|---|---|---|
| 5,110,293 A | 5/1992 | Linkow |
| 5,116,226 A | 5/1992 | Linkow |
| 5,141,435 A | 8/1992 | Lillard |
| 5,302,128 A | 4/1994 | Suga |
| 5,800,168 A | 9/1998 | Cascione et al. |
| 5,871,356 A | 2/1999 | Guedj |
| 5,989,030 A | 11/1999 | Suga |
| 6,692,254 B1 | 2/2004 | Kligerman et al. |
| 7,059,856 B2 | 6/2006 | Marotta |
| 8,038,442 B2 | 10/2011 | Hurson |
| 8,714,977 B2 | 5/2014 | Fromovich et al. |
| 9,387,027 B2 | 7/2016 | Yahav |
| 2005/0152770 A1 | 7/2005 | Tschakaloff et al. |
| 2006/0147880 A1 | 7/2006 | Krumsiek et al. |
| 2006/0241623 A1 | 10/2006 | Lim et al. |
| 2008/0280254 A1 | 11/2008 | Ackermann |
| 2010/0112523 A1 | 5/2010 | Fromovich et al. |
| 2016/0151173 A1* | 6/2016 | Iannotti .............. A61B 17/8802 606/86 R |

FOREIGN PATENT DOCUMENTS

| | | |
|---|---|---|
| JP | 2011-104222 | 2/2011 |
| WO | WO95/24165 | 9/1995 |
| WO | WO 2015/050331 | 4/2015 |

* cited by examiner

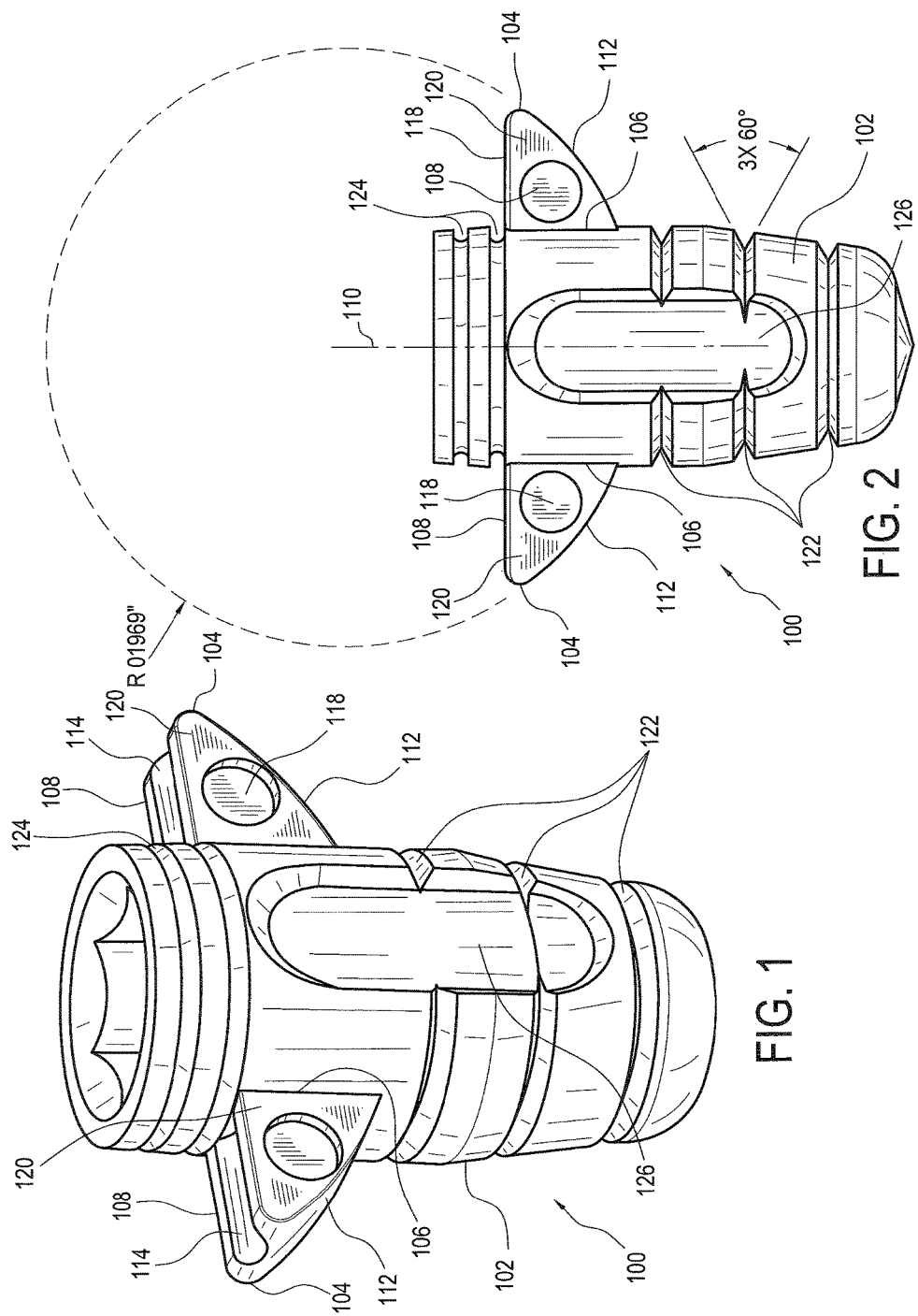

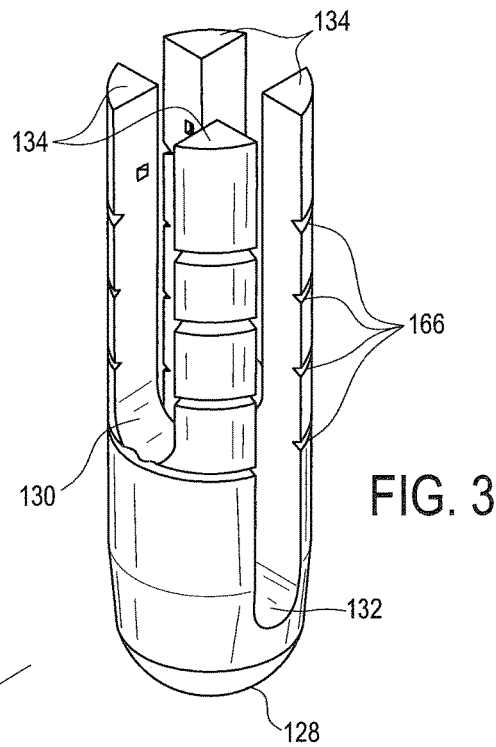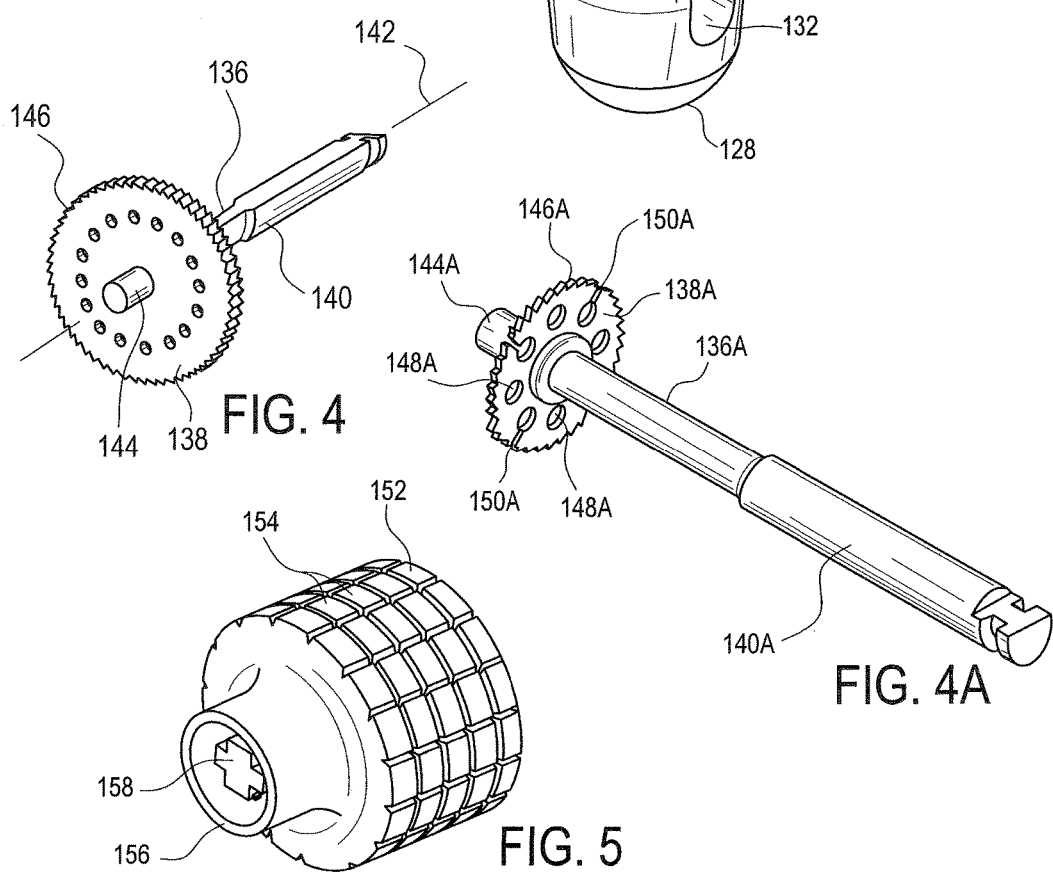

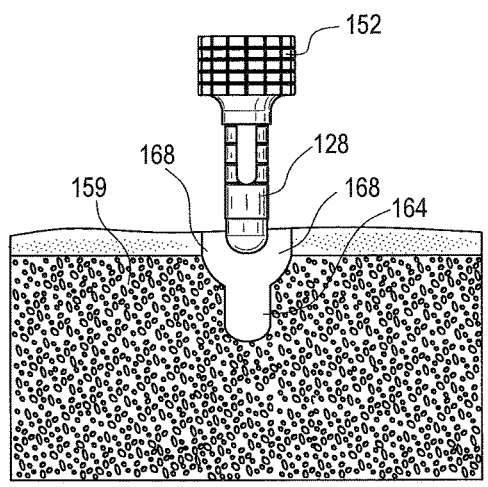
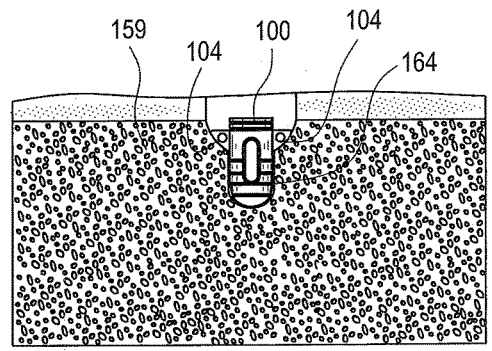
FIG. 14   FIG. 15
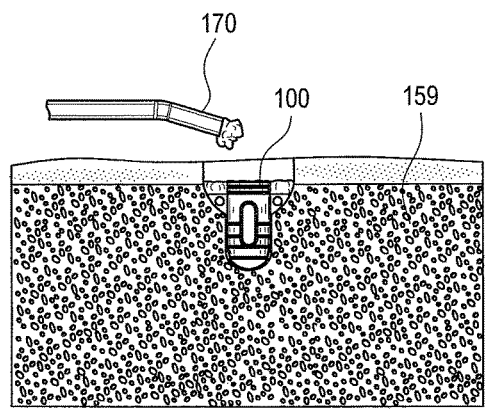
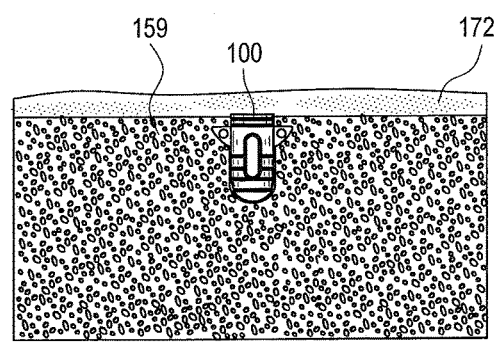
FIG. 16   FIG. 17

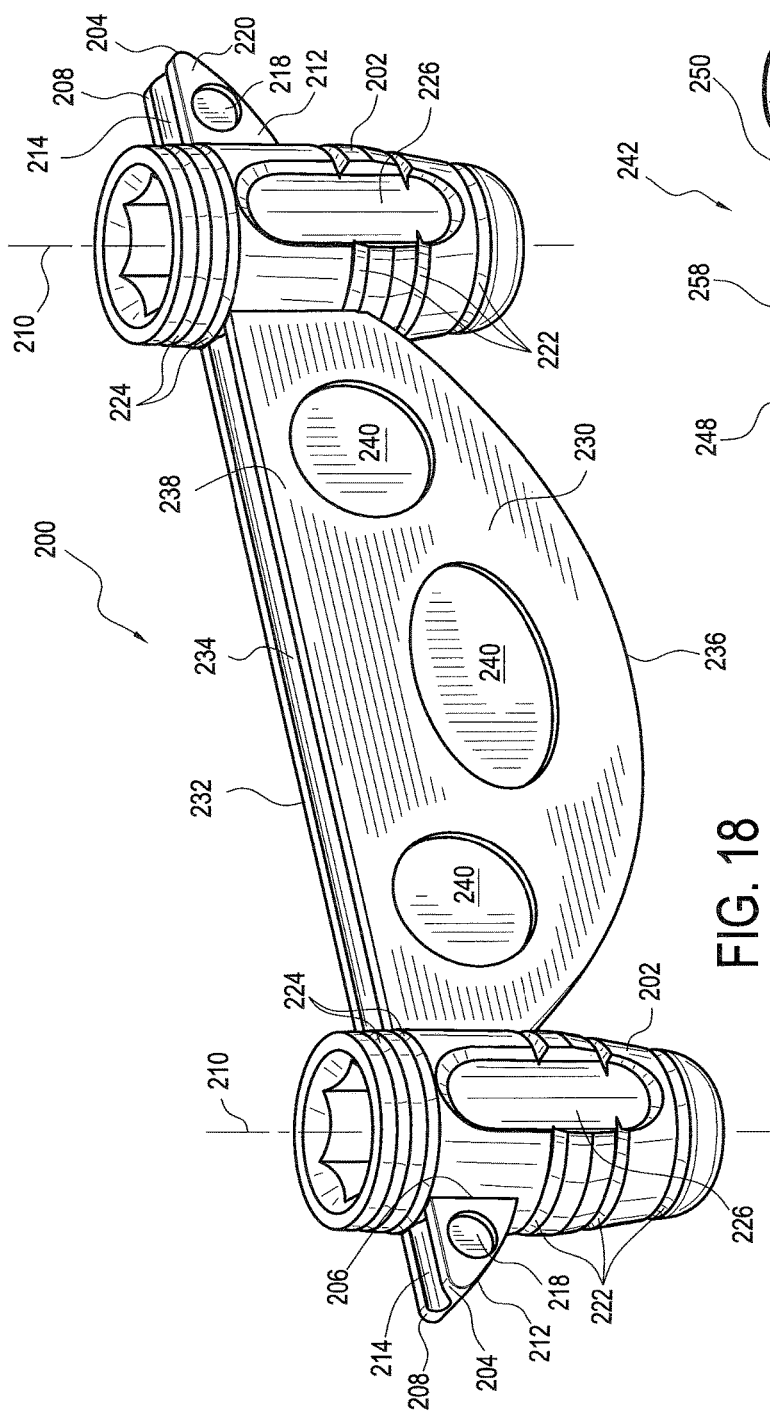
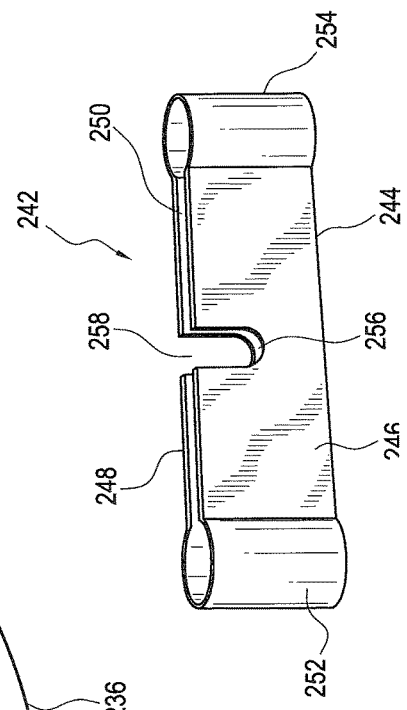
FIG. 18
FIG. 19

SYSTEM OF COMPONENTS OR IMPLEMENTS FOR EASILY AND PRECISELY INSTALLING A DENTAL IMPLANT, AND A METHOD OF INSTALLING THE DENTAL IMPLANT

FIELD OF THE INVENTION

The present invention relates generally to dental implants, and more particularly to a system of components for precisely installing a dental implant. It is noted that this patent application is related to U.S. patent application Ser. No. 15/261,129 which was filed in the United States Patent Office on Sep. 9, 2016. While the aforenoted patent application is concerned with the dental implant itself, which comprises either a single implant having wing members projecting outwardly from diametrically opposite external sidewall portions thereof, or a dual implant comprising, in effect, a pair of single implants connected together by means of a connective bar or plate, and wherein each one of the pair of single implants has a single wing member projecting outwardly from a laterally external side wall portion of each single implant effectively forming the dual implant, the present invention is concerned with a system of components or implements which render the installation of the implants to be performed and achieved in an easy yet precise manner.

BACKGROUND OF THE INVENTION

As been noted hereinbefore, the above-identified, previously filed United States Patent Application is concerned with a dental implant which has a substantially cylindrical configuration and a pair of wing members projecting outwardly from diametrically opposite side wall portions of the implant. The wing members have a substantially right triangular configuration with one leg of each right triangle effectively connecting the wing member to the body of the implant, the other leg of the right triangle extending outwardly from the body of the implant at an orientation that is perpendicular to the longitudinal axis of the implant body, and the hypotenuse side of the right triangle being radiused so as to promote osseointegration. In addition, or as a second embodiment of a dental implant, two single winged implants are effectively connected together by means of a connecting bar or plate. In accordance with this dual implant, the wing members are only provided upon the laterally external side wall portions of each single implant while the oppositely disposed internal portions of each implant are integrally connected to the intermediary connecting bar or plate. The undersurface of the connecting bar or plate is likewise radiused so as to promote osseointegration.

Various prior art patent publications have been cited within the aforenoted, previously filed United States Patent Application, wherein such prior art is directed toward various single and dual or multiple implants, however, while the various prior art patent publications disclose various dental implants comprising diverse structures, it is noted that in connection with those patent publications directed toward a single implant, none of the implants comprise structure which is specifically oriented toward providing or promoting both physical stability and structural stability by means of enhancing, for example, osseointegration, which is critically important to the success of the implant becoming an integrally fixed part of a person's set of teeth. This is likewise seen to be the case in connection with an implant structure comprising multiple implants connected together by means of a connective bar, plate, or similar structure. Still yet further, none of the prior art referenced within the aforenoted, previously filed patent application is directed a system of components or implements for easily and precisely installing the dental implants.

A need therefore exists in the art for a new and improved system of components or implements for easily and precisely installing a single dental implant, and/or a dual implant comprising, for example, a pair of single implants which are connected together by means of a bar, plate, or similar structure, such that, once installed, the implant structure will exhibit both physical and structural stability such that the implant structure successfully becomes an integrally fixed part of the person's set of teeth as a result of various structural features of the implant structure which will promote osseointegration, wherein osseointegration is well-known to be defined as that state wherein there is no progressive relative movement between the implant and the bone with which it is directly connected.

OVERALL OBJECTIVES OF THE INVENTION

It is an overall objective of the present invention to provide a new and improved system of components or implements for easily and precisely installing a single implant, or a dual implant comprising, for example, a pair of single implants which are connected together by means of a bar, plate, or similar structure, which will provide the implant structure with both physical and structural stability such that the implant structure successfully becomes an integrally fixed part of the person's set of teeth as a result of various structural features of the implant structure which will promote osseointegration, wherein osseointegration is well-known to be defined as that state wherein there is no progressive relative movement between the implant and the bone with which it is directly connected.

SUMMARY OF THE INVENTION

The foregoing and other objectives are achieved in accordance with the teachings and principles of the present invention through the provision of a new and improved system of components or implements for easily and precisely installing a single implant, or a dual implant comprising, for example, a pair of single implants which are connected together by means of a bar, plate, or similar structure. The system comprises an implant rotary cutter guide which substantially comprises a cylindrical structure which is closed or solid at the lower or bottom end portion thereof and which is adapted to be inserted into a blind bore drilled within a particular section or location of the patient's jaw within which the dental implant is to be ultimately disposed, seated, and secured. The diametrical extent of the implant rotary cutter guide is precisely the same as the diametrical extent of the dental implant which is to be ultimately disposed, seated, and secured within the drilled blind bore. Still further, the central and upper portions of the cylindrical rotary cutter guide are effectively defined by means of four upstanding arcuately configured side wall portions comprising two pairs of diametrically opposed arcuately configured side wall portions. More particularly, the four upstanding arcuately configured side wall portions of the central and upper portions of the cylindrical implant rotary cutter guide are defined or created by means of a first vertically extending slot passing through the central and upper portions of the cylindrical implant rotary guide such that the first vertically extending through-slot is oriented along a first diametrical plane passing through the cylindrical implant rotary cutter guide. This first vertically and diametrically extending through-slot also terminates at an elevational level that is substantially midway between the closed lower or bottom end portion of the cylindrical implant rotary cutter guide and the upper open end portion of the cylindrical implant rotary cutter guide. Still further, the central and upper portions of the cylindrical implant rotary cutter guide have a second vertically oriented slot passing through the central and upper portions of the cylindrical implant rotary cutter guide such that the second vertically extending through-slot is oriented along a second diametrical plane which passes through the cylindrical implant rotary cutter guide and is oriented substantially perpendicular to the first diametrical plane within which the first vertically and diametrically extending through-slot is disposed. This second vertically and diametrically extending through-slot is longer than the first vertically and diametrically extending through-slot such that this second vertically and diametrically extending through-slot extends beneath the midway elevational level of the cylindrical implant rotary cutter guide as defined between the bottom or lower closed end of the cylindrical implant rotary cutter guide and the upper open end of the cylindrical implant rotary cutter guide.

A rotary cutter, comprising a planar cutting disk having a circular configuration, is fixedly mounted upon one end of an axially oriented support post or axle wherein the opposite end of the support post or axle is adapted to be operatively connected to a rotary actuator so as to rotate the rotary cutter around its axis and therefore cut a slot within a section of a patient's jaw. A portion of the support post or axle projects axially through the planar rotary cutting disk such that a stub portion of the support post or axle projects axially away from the planar rotary cutting disk and extends in an axial direction perpendicular to the oppositely disposed faces of the planar rotary cutting disk. The circumferential peripheral surface of the planar rotary cutting disk is provided with a plurality of cutting teeth so as to achieve the cutting operation to be performed in connection with the installation of the dental implant. When the rotary cutter is adapted to be utilized in conjunction with the cylindrical implant rotary cutter guide, the planar rotary cutting disk of the planar rotary cutter is inserted into the second vertically and diametrically extending through-slot defined within the cylindrical rotary cutter guide, while at the same time, the support post or axle of the rotary cutter is inserted into the first vertically and diametrically extending through-slot defined within the cylindrical rotary cutter guide such that the support post or axle projects axially outwardly through one end of the first vertically and diametrically extending through-slot defined within the cylindrical rotary cutter guide while the stub portion of the support post or axle projects axially outwardly through a second diametrically opposite end of the first vertically and diametrically extending through-slot defined within the cylindrical rotary cutter guide.

Since the first vertically and diametrically extending through-slot is the shorter one of the first and second vertically and diametrically extending through-slots defined within the cylindrical rotary cutter guide, the support post or axle and the stub portion of the support post or axle will encounter the bottom or lowermost end portions of the first vertically and diametrically extending through-slot defined within the cylindrical rotary cutter guide such that the rotary cutter cannot effectively be inserted any further into the cylindrical rotary cutter guide as considered in the downward direction, however, since the planar rotary cutting disk of the rotary cutter is disposed within the second longer one of the first and second vertically and diametrically extending through-slots defined within the cylindrical rotary cutter guide, outer peripheral cutting edge portions of the rotary cutting disk can in fact extend radially beyond the external circumferential surface of the cylindrical rotary cutter guide as well as vertically below the elevational level at which further insertion of the rotary cutter has been terminated as a result of the support post or axle and stub portion of the support post or axle encountering the bottom or lowermost end portions of the first vertically and diametrical extending through-slot defined within the cylindrical rotary cutter guide. In this manner, radiused slots are effectively cut into bone portions of the patient's jaw upon opposite sides of the cylindrical rotary cutter guide so as to be able to accommodate the wing members of the dental implant.

In a similar manner, when it is desired to insert a dual implant into a patient's jaw, a dual implant rotary cutter guide assembly is utilized. More particularly, the dual implant rotary cutter guide assembly is seen to comprise a transversely oriented rotary cutting disk guide which comprises a central portion which has two parallel plates that are spaced apart from each other a sufficient distance so as to define a transversely extending slot which is slightly larger than the thickness dimension of the planar rotary cutting disk whereby the planar rotary cutting disk can in fact be accommodated within the transversely oriented slot defined between the two parallel plates of the transversely oriented rotary cutting disk guide. Opposite ends of the two spaced parallel plates are effectively joined together so as to form two annular ring members which are integrally connected to the two spaced parallel plates. The two annular ring members have diametrical extents that are sufficient to accommodate a pair of cylindrical rotary cutter guides, similar to those used in connection with the installation of a single winged implant, when the two annular ring members are effectively disposed over the upper end portions of the pair of cylindrical rotary cutter guides such that the two annular ring members respectively surround each one of the pair of cylindrical rotary cutter guides.

Still further, the second vertically and diametrically extending through-slots defined within each one of the pair of cylindrical rotary cutter guides are disposed such that the second vertically and diametrically extending through-slots of the pair of cylindrical rotary cutter guides are disposed within the same plane as the transversely oriented slot defined between the pair of transversely oriented parallel plates of the transversely oriented slot defined within the transversely oriented rotary cutting disk guide. In this manner, when the rotary cutting disk is inserted into the transversely oriented slot defined within the transversely oriented rotary cutting disk guide, oppositely disposed circumferential or peripheral side cutting portions of the rotary cutting disk can be accommodated within the second vertically and diametrically extending through-slots defined within the pair of cylindrical rotary cutter guides. Accordingly, the rotary cutting disk can then be utilized to form the radiused slot within the patient's jawbone for accommodating the connecting bar or plate of the dual implant. As was the case with each one of the cylindrical rotary cutter guides, each one of the pair of transversely oriented parallel plates of the transversely oriented rotary cutting disk guide is provided with a slot or notch within the central upper edge portion of each plate for accommodating the support post or axle of the rotary cutting disk as well as the stub portion of the support post or axle so as to predetermine or precisely limit the extent to which the rotary cutting disk can be moved downwardly relative to the transversely oriented rotary cutting disk guide, the pair of cylindrical rotary cutter guides, and the patient's jawbone. In this manner, the depth of the radiused slot, defined within the patient's jawbone for accommodating the transversely oriented connecting plate or bar of the dual dental implant, is precisely defined and predetermined.

BRIEF DESCRIPTION OF THE DRAWINGS

Various other features and attendant advantages of the present invention will be more fully appreciated from the following detailed description when considered in connection with the accompanying drawings in which like reference characters designate like or corresponding parts throughout the several views, and wherein:

FIG. 1 is a perspective view of a single implant to be implanted into a patient's jaw in accordance with the system and method embodying the principles and teachings of the present invention;

FIG. 2 is a side elevational view of the single implant as disclosed within FIG. 1;

FIG. 3 is a perspective view of the new and improved cylindrical rotary cutter guide as constructed in accordance with principles and teachings of the present invention;

FIG. 4 is a perspective view of a first embodiment of a rotary cutter as constructed in accordance with the principles and teachings of the present invention;

FIG. 4A is a perspective view of a second alternative embodiment of a rotary cutter as constructed in accordance with the principles and teachings of the present invention;

FIG. 5 is a perspective view of a handpiece component or implement which is utilized to grasp the cylindrical rotary cutter guide as shown in FIG. 3 so as to manipulate the same during insertion of the rotary cutter guide into a blind bore formed at the implant side so that a rotary cutter, as illustrated within FIG. 4 or 4A, can be utilized to form slots within bone portions of the patient's jaw adjacent to the implant site in order to properly house or accommodate the single winged implant as illustrated within FIGS. 1 and 2;

FIGS. 6-17 are a series of schematic drawings illustrating the method of installing a single winged implant into the jaw bone of a patient at a dental implant site, wherein the method comprises the steps of forming a blind bore within the jaw bone of a patient at the designated implant site by means of a plurality of drill bits, inserting the cylindrical rotary cutter guide, as illustrated within FIG. 3, into the blind bore in preparation for receiving the rotary cutting disk, as shown in FIG. 4, inserting the rotary cutter into the cylindrical rotary cutter guide such that the rotary cutting disk cuts into the patient's jaw bone and forms slots upon opposite sides of the blind bore for accommodating the single winged implant, as illustrated within FIGS. 1 and 2, removing the rotary cutting disk from the rotary cutter guide, removing the rotary cutter guide from the blind bore, inserting the single winged implant into the blind bore of the implant site, inserting bone allograft onto the top of the implant site in order to begin and facilitate the osseointegration process, and suturing the patient's gum so as to close the implant site;

FIG. 18 is a perspective view of a dual winged implant to be implanted within a patient's jaw wherein a pair of single implants, similar to the single implant shown in FIGS. 1 and 2, are effectively fixedly secured to opposite ends of an intermediary connecting bar or plate; and FIG. 19 is a perspective view of a second embodiment of a new and improved rotary cutter guide as constructed in accordance with principles and teachings of the present invention and adapted to be utilized in conjunction with the easy and precise installation of a dual winged implant as illustrated within FIG. 18.

DETAILED DESCRIPTION OF THE ILLUSTRATED EMBODIMENTS

Figures 6, 7:
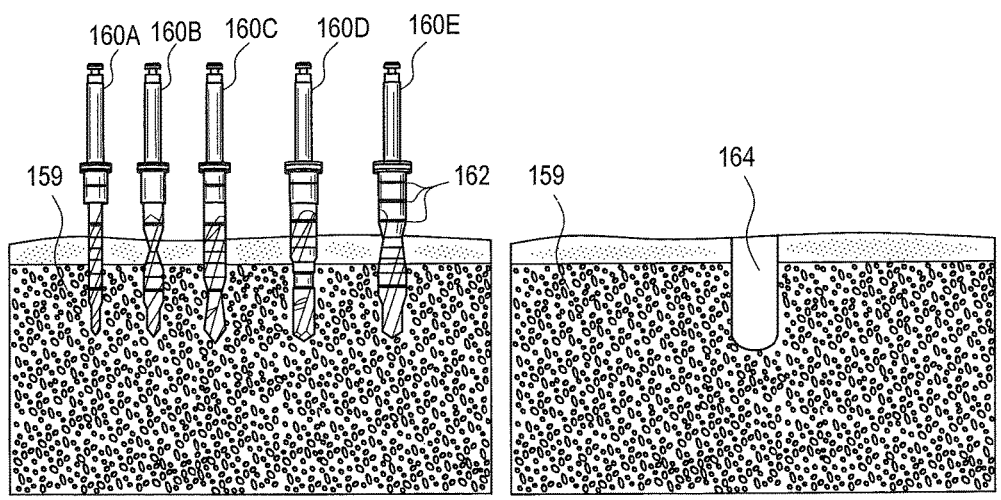
Figures 8, 9:
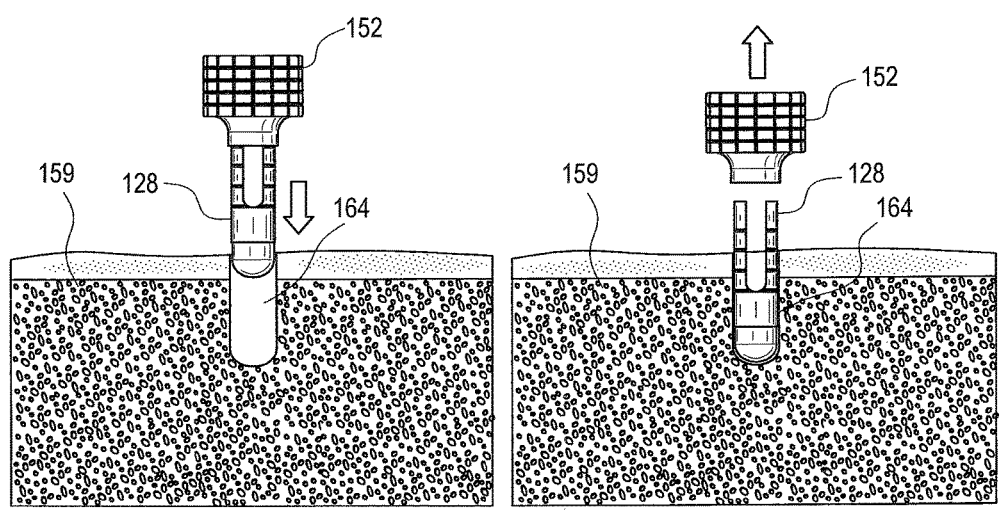
Figure 10:
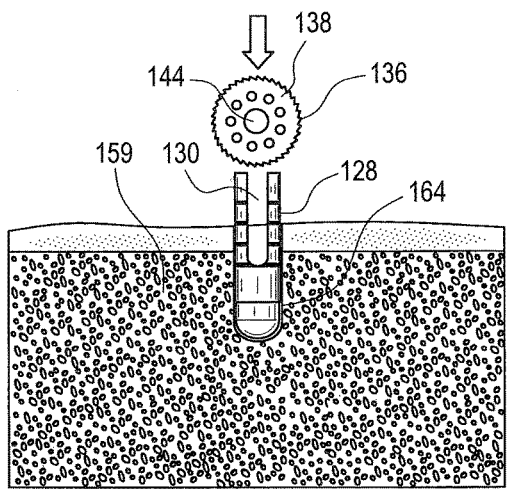
Figure 11:
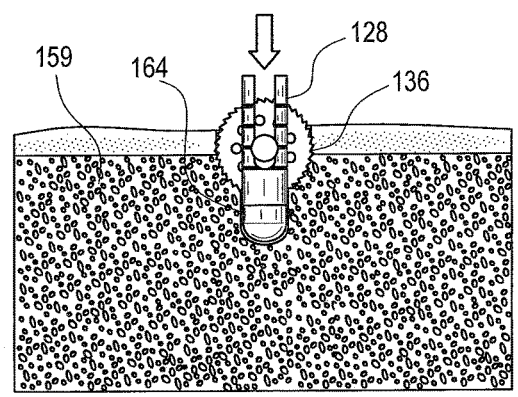
Figure 12:
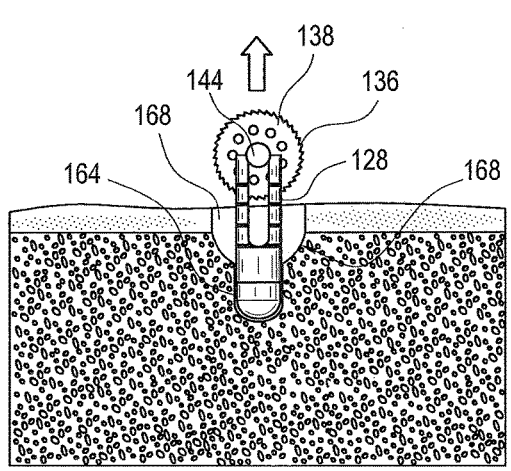

Referring now to the drawings, and more particularly to FIGS. 1 and 2 thereof, there is disclosed a single dental implant which is generally indicated by the reference character 100 and which is adapted to be implanted within one or both of the maxillary or upper jaw bone and the mandible or lower jaw bone of a patient's mouth in accordance with the system and method embodying the principles and teachings of the present invention. More particularly, the winged implant 100 is seen to comprise a substantially cylindrical body portion 102 which is to be implanted within one of the jaw bones of the patient, and that the opposite end of the implant 100 is adapted to have an abutment fixedly secured thereon such that a dental crown can be fixedly secured to the abutment. The substantially cylindrical body portion 102 of the single dental implant 100 has a substantially cylindrical configuration, and a pair of wings 104,104 project radially outwardly from oppositely disposed external side wall portions of the implant body portion 102. The wing members 104 each have a substantially right triangular configuration with the vertically oriented leg 106 of each right triangle effectively connecting the wing member 104 to the cylindrical body portion 102 of the implant 100, while the horizontally oriented leg 108 of each right triangle extends outwardly from the body portion 102 of the implant 100 at an orientation that is substantially perpendicular to the longitudinal axis 110 of the implant body portion 102. Lastly, the hypotenuse side 112 of each one of the right triangles of each wing member is radiused with a radius dimension of, for example, 0.1969 inches (0.1969") as can be seen in FIG. 2.

A linear groove 114 is formed within the upper edge portion of each one of the horizontally oriented legs 108 of the wing members, and a similar groove, not shown, can be formed within the external radiused edge portion of the hypotenuse side 112 of each one of the wing members 104,104. In addition, recesses 118, having circular configurations, although other geometrical configurations are possible, are formed within opposite side surfaces 120 of the wing members 104. Still yet further, circumferential or annular ring members or cavities 122 are formed within the central and lower external surface portions of the implant body 102. As can be seen from FIG. 2, the annular or circumferential ring members 122 subtend angular extents of 60°. Additional annular or circumferential ring members or cavities 124 are defined within the upper external surface portions of the implant body 102. The annular or circumferential ring members 122,124 are provided so as to effectively interrupt the transmission of impact forces that are generated during the chewing of food, and both sets of annular or circumferential rings members 122,124 serve to permit bone tissue to build up within such cavities so as to effectively define bone connections to the implant 100 in order to firmly affix the implant 100 within the particular jaw bone as a result of osseointegration. Still further, in addition to the circular recesses 118 defined upon the wing members 104, an elliptically configured recess 126, having its longitudinal axis disposed parallel to the longitudinal axis 110 of the implant body 102, is defined upon diametrically opposite external portions of the implant body 102. The recesses 118,126 serve to reduce stress forces which would otherwise be developed between the bone and the implant 100 because the bone has spatial areas within which to grow and regenerate. Bone morphogenic protein-2 (BMP-2) is also adapted to be disposed within the various recesses 118,126 defined upon the wing members 104, 104 and the implant body 102. The bone morphogenic protein-2 (BMP-2) promotes or stimulates the generation of osteoblasts which enhance bone regeneration.

Continuing further, it is also to be noted that the wing members 104, 104, and the radiused hypotenuse edge portions 112,112 thereof serve additional functions important to the overall structure of the new and improved implant 100 as well as its successful implantation within the upper or lower jaw 10,12. More particularly, after a substantially cylindrical hole is formed within the particular upper or lower jaw bone so as to accommodate the cylindrical body portion 102 of the implant 100, radiused slots, not shown, are also formed within the particular jaw bone in a transverse manner crossing the hole in the jaw bone for accommodating the cylindrical body portion 102 of the implant 100, so as to accommodate the wing members 104,104. As will be discussed more fully hereinafter, such radiused slots, not shown, may be formed by means of a suitable rotary cutting disk. The size of the rotary cutting disk is of course to be such as to correspond to the radiused hypotenuse edge portions 112 of the wing members 104, that is, the 0.1969 inches (0.1969"). As can therefore be appreciated, when the implant 100 is in fact inserted into the particular upper or lower jaw bone, not only is the cylindrical body portion 102 of the implant 100 accommodated within its cylindrical hole formed within the particular jaw bone, but the pair of wing members 104,104 are now disposed within their radiused slots. It can therefore be appreciated that the wing members 104,104 provide physical stability for the implant 100 with respect to it disposition within the particular jaw bone in that the wing members 104,104 will effectively resist not only linear forces perpendicular to the surfaces 120,120 thereof, but also rotational forces tending to rotate the implant 100 within its cylindrical hole or bore. Still yet further, the various grooves, recesses, and circumferential ring members serve as sites within which bone regeneration is permitted to flourish so as to promote osseointegration whereby the implant will in fact be integrally connected to the maxillary or mandible jaw bone within which it is implanted. In particular, the provision of the radiused slots, not shown, for accommodating the radiused hypotenuse edge portions 112, 112 of the wing members 104,104 enhance bone growth and osseointegration because bone growth prefers sloped or smoothly radiused or curved surfaces upon which to generate.

Having described the single dental implant, reference is now made to the unique and novel system of components or implements, as constructed in accordance with the principles and teachings of the present invention, for easily and precisely installing the single dental implant within a jaw bone of a patient. More particularly, with reference initially being made to FIGS. 3 and 4, the system for easily and precisely installing an implant, such as, for example, the implant 100, within a patient's jaw, is seen to comprise an implant rotary cutter guide 128, as best seen in FIG. 3, which substantially comprises a cylindrical structure that is closed or solid at the lower or bottom end portion thereof and which is adapted to be inserted into a blind bore drilled within a particular section or location of the patient's jaw within which the dental implant is to be ultimately disposed, seated, and secured, as will be described more fully hereinafter. The diametrical extent of the implant rotary cutter guide 128 is precisely the same as the diametrical extent of the cylindrical body portion 102 of the dental implant 100 which is to be ultimately disposed, seated, and secured within the drilled blind bore. Still further, the central and upper portions of the cylindrical rotary cutter guide 128 are effectively defined by means of four (4) upstanding arcuately configured side wall portions comprising two pairs of diametrically opposed arcuately configured side wall portions. More particularly, the four upstanding arcuately configured side wall portions of the central and upper portions of the cylindrical implant rotary cutter guide 128 are defined or created by means of a first vertically extending slot 130 which passes through the central and upper portions of the cylindrical implant rotary cutter guide 128 such that the first vertically extending through-slot 130 is oriented along a first diametrical plane passing through the cylindrical implant rotary cutter guide 128.

This first vertically and diametrically extending through-slot 130 also terminates at an elevational level that is substantially midway between the closed lower or bottom end portion of the cylindrical implant rotary cutter guide 128 and the upper open end portion of the cylindrical implant rotary cutter guide 128. Still further, the central and upper portions of the cylindrical implant rotary cutter guide 128 have a second vertically oriented slot 132 passing through the central and upper portions of the cylindrical implant rotary cutter guide 128 such that the second vertically extending through-slot 132 is oriented along a second diametrical plane that passes through the cylindrical implant rotary cutter guide 128 and is oriented substantially perpendicular or orthogonal to the first diametrical plane within which the first vertically and diametrically extending through-slot 130 is disposed. It can therefore be appreciated that the first and second vertically extending through-slots 130, 132 effectively divide the rotary cutter guide 128 into four (4) circumferentially spaced, upstanding leg portions 134 wherein each upstanding leg portion 134 has a substantially right-triangular cross-sectional configuration with the external hypotenuse portions of each leg portion 134 having an arcuate configuration coinciding with the overall cylindrical configuration of the rotary cutter guide 128. In addition, it is noted that this second vertically and diametrically extending through-slot 132 is longer than the first vertically and diametrically extending through-slot 130 such that this second vertically and diametrically extending through-slot 132 extends beneath the midway elevational level of the cylindrical implant rotary cutter guide 128 as defined between the bottom or lower closed end of the cylindrical implant rotary cutter guide 128 and the uppermost open end portion of the cylindrical implant rotary cutter guide 128. Likewise, it is seen that the width of the first vertically and diametrically extending through-slot 130 is relatively greater than the width of the second vertically and diametrically extending through-slot 132 for reasons that will become apparent hereinafter.

Continuing further, and with reference being made to FIG. 4, a first embodiment of a rotary cutter 136 is disclosed and is seen to comprise a planar cutting disk 138 which has a circular configuration and is fixedly mounted upon one end of an axially oriented support post or axle 140 wherein the opposite end of the support post or axle is adapted to be operatively connected to a rotary actuator, not shown, so as to rotate the rotary cutter 136 around its longitudinal axis 142 and therefore cut a slot within a section of a patient's jaw. A portion of the support post or axle projects axially through the planar rotary cutting disk 138 such that a stub portion 144 of the support post or axle 140 projects axially away from the planar rotary cutting disk 138 and extends in an axial direction perpendicular to the oppositely disposed faces of the planar rotary cutting disk 138. The circumferential peripheral surface of the planar rotary cutting disk 138 is provided with a plurality of cutting teeth 146 so as to achieve the cutting operation to be performed in connection with the installation of the dental implant 100. When the rotary cutter 136 is adapted to be utilized in conjunction with the cylindrical implant rotary cutter guide 128, the planar rotary cutting disk 138 of the planar rotary cutter 136 is inserted into the second vertically and diametrically extending through-slot 132 defined within the cylindrical rotary cutter guide 128, while at the same time, the support post or axle 140 of the rotary cutter 136 is inserted into the first vertically and diametrically extending through-slot 130 defined within the cylindrical rotary cutter guide 128 such that the support post or axle 140 projects axially outwardly through one end of the first vertically and diametrically extending through-slot 130 defined within the cylindrical rotary cutter guide 128 while the stub portion 144 of the support post or axle 140 projects axially outwardly through a second diametrically opposite end of the first vertically and diametrically extending through-slot 130 defined within the cylindrical rotary cutter guide 128. This is extremely important in that the disposition of the support post or axle 140 projecting axially outwardly through a first end of the first vertically and diametrically extending through-slot 130 defined within the cylindrical rotary cutter guide 128, while the stub portion 144 of the support post or axle 140 projects axially outwardly through a second diametrically opposite end of the first vertically and diametrically extending through-slot 130 defined within the cylindrical rotary cutter guide 128, provides inherent stability to the rotary cutter 136, and particularly to the rotary cutting disk 138, when mounted within the cylindrical rotary cutter guide 128, such that clean, crisp, and accurate slots can in fact be formed within the patient's jaw bone for forming the slots which will accommodate the oppositely disposed winged members 104,104 of the implant 100, as will be discussed more fully hereinafter.

Since the first vertically and diametrically extending through-slot 130 is the shorter one of the first and second vertically and diametrically extending through-slots 130,132 defined within the cylindrical rotary cutter guide 128, the support post or axle 140 and the stub portion 144 of the support post or axle 140 will encounter the bottom or lowermost end portions of the first vertically and diametrically extending through-slot 130 defined within the cylindrical rotary cutter guide 128 such that the rotary cutter 136 cannot effectively be inserted any further into the cylindrical rotary cutter guide 128 as considered in the downward direction, however, since the planar rotary cutting disk 138 of the rotary cutter 136 is disposed within the second longer one 132 of the first and second vertically and diametrically extending through-slots 130,132 defined within the cylindrical rotary cutter guide 128, outer peripheral cutting edge portions of the rotary cutting disk 138 will in fact extend radially beyond the external circumferential surface of the cylindrical rotary cutter guide 128 as well as vertically below the elevational level at which further insertion of the rotary cutter 136 has been terminated as a result of the support post or axle 140 and the stub portion 144 of the support post or axle 140 encountering the bottom or lowermost end portions of the first vertically and diametrical extending through-slot 130 defined within the cylindrical rotary cutter guide 128. In this manner, radiused slots are effectively cut into bone portions of the patient's jaw upon opposite sides of the cylindrical rotary cutter guide 128 so as to be able to accommodate the wing members 104 of the single dental implant 100.

A second embodiment of a rotary cutter that may be employed, in a manner similar to that of the rotary cutter 136 as illustrated within FIG. 4, is illustrated within FIG. 4A as at 136A. The only significant differences between the two rotary cutters 136,136A resides in the fact that the rotary cutting disk 138A of the rotary cutter 136A is provided with a series of holes or apertures 148A disposed within a circumferential array, and still further, the rotary cutting disk 138A also has a plurality of substantially radially extending slots 150A which extend from the peripheral edge portion of the rotary cutting disk 138A, as defined by means of cutting teeth 146A, to the holes or apertures 148A. These holes or apertures 148A and the substantially radial slots 150A effectively provide escape routes or paths for bone debris which will be gene-rated by means of the rotary cutting disk 138A when the slots are cut within those areas of the patient's jaw bone adjacent to the implant site in order to accommodate the winged portions 104 of the winged implant 100. The remaining structural parts of the rotary cutter 136A that have not been discussed in detail are substantially the same as, and function in a manner similar to corresponding parts of the rotary cutter 136 and have therefore been provided with corresponding reference numbers followed by the letter A.

Lastly, with reference being made to FIG. 5, in order to accomplish the easy and precise installation of a single dental implant 100 within a patient's jaw, one additional component or implement of the system of the present invention is disclosed. More particularly, it is seen that a handpiece 152 is adapted to be grasped by means of, for example, a dental technician or dental doctor, whereby the handpiece 152 will serve to, in turn, grasp, and lock on to, the upper end portion of the cylindrical rotary cutter guide 128 in order to facilitate the insertion of the cylindrical rotary cutter guide 128 into a blind bore drilled into the patient's jaw at the dental implant site, as well as to remove the cylindrical rotary cutter guide 128 from the blind bore when the preparatory slot-cutting operations have been completed whereby the dental implant site is then ready to receive the single winged implant 100. As can be seen in FIG. 5, the handpiece 152 comprises an upper cylindrical housing 154 which effectively serves a handle by means of which the handpiece 152 may in fact be grasped and firmly held, and a lower cylindrical connector portion 156 which projects axially downwardly from the handpiece/handle 154 in a coaxial manner.

A male connector 158, having the configuration of a cruciform, is fixedly secured to an internal portion of the connector portion 156 wherein it can be seen that the two crosspieces of the male connector 158 have different width dimensions. The crosspiece of the male connector 158 having the larger width dimension is adapted to be inserted into or engaged within the upper end portion of the first vertically and diametrically extending through-slot 130 defined within the cylindrical rotary cutter guide 128 while the crosspiece of the male connector 158 having the smaller width dimension is adapted to be inserted into or engaged within the upper end portion of the second vertically and diametrically extending through-slot 132 defined within the cylindrical rotary cutter guide 128. In this manner, the handle/handpiece 152 is effectively rotatably fixed upon the upper end portion of the cylindrical rotary cutter guide 128 from a relative rotational point of view, that is, the handle/handpiece 152 cannot be rotatably moved with respect to the cylindrical rotary cutter guide 128. In addition, latching members, not shown but which may take the form of, for example, spring-biased latches, detent balls, or the like, are also disposed internally within the open end, portion of the connector portion 156 so as to effectively cooperate with corresponding structure disposed upon the upper external circumferential surface portion of the cylindrical rotary cutter guide 128 such that when such cooperative latching structure is engaged, the handle or handpiece 152 is locked onto the upper end portion of the cylindrical rotary cutter guide 128 so as to in fact enable manipulation of the cylindrical rotary cutter guide 128 into and out from the blind bore formed within the patient's jaw in order to facilitate the proper insertion of the single winged implant 100 within the patient's jaw as will be discussed more fully hereinafter.

In order to render the foregoing description of the unique and novel, and new and improved, system of components or implements of the present invention, for installing a single dental implant 100 within a predetermined site defined within the jaw bone of a patient, even more readily understandable, the method of easily and precisely installing the dental implement, utilizing the system of components or implements of the present invention, will now be described with reference being made to FIGS. 6-17. More particularly, as can readily be appreciated from FIG. 6, the first step of the implant installation process is to drill a hole or bore at the designated implant site within the bone 159 of a patient. As illustrated within FIG. 6, the drilling operation is performed by using, for example, a series of drill bits 160A-E wherein the drill bits 160A-E are progressively larger in their diametrical extents. By utilizing progressively larger diameter drill bits, the drilling operation is effectively rendered easier and quicker to accomplish because the initial drilled bore does not remove a relatively large amount of bone, and then as a result of the use of the progressively larger diameter drill bits, bone matter is progressively removed as opposed to the removal of a relatively large amount of bone matter during a single drilling operation. It is of course also to be understood that, for example, five bores are not in fact drilled, FIG. 6 merely illustrating the use of a plurality of drill bits 160A-E so as to illustrate the step-wise drilling procedure utilizing drill bits having progressively larger diametrical extents. It is also noted that each one of the drill bits 160A-E has a plurality of vertically spaced circumferential markings or lines 162 disposed upon external peripheral surface portions of each drill bit 160A-E so as to effectively indicate the depth to which the bore is being drilled.

Once the bore 164, as illustrated within FIG. 7, has been drilled to the proper size and depth by means of the different drill bits 160A-E, the bore 164 is ready to receive the cylindrical rotary cutter guide 128. Accordingly, as illustrated within FIG. 8, the assembly, comprising the cylindrical rotary cutter guide 128 and the handle/handpiece 152 which has been fixedly mounted the upper end portion of the cylindrical rotary cutter guide 128 as has been described hereinbefore, is then moved downwardly so as to insert and deposit the cylindrical rotary cutter guide 128 into the drilled bore 164 until the bottom or closed end portion of the cylindrical rotary cutter guide 128 is fully inserted into the drilled bore 164 as a result of the bottom or closed end portion of the cylindrical rotary cutter guide 128 encountering the bottom of the blind bore 164. When this is achieved, the handle or handpiece 152 is disengaged from the cylindrical rotary cutter guide 128, and for now, placed aside, while the cylindrical rotary cutter guide 128 of course remains within the bottom portion of the drilled bore 164 as illustrated within FIG. 9. It is to be noted that in addition to the vertically spaced markings or indicia 162 defined upon the drill bits 160A-E so as to determine the precise depth to which the blind bore 164 is to be drilled, the outer peripheral or circumferential surface of the cylindrical rotary cutter guide 128 is likewise provided with a plurality of vertically spaced markings or indicia lines 166, as can best be seen in FIG. 3, which are likewise utilized to confirm that when the cylindrical rotary cutter guide 128 is in fact fully inserted into the drilled bore 164, it is disposed or located at precisely the correct depth for it to be utilized in conjunction with the rotary cutter 136.

Figure 13:
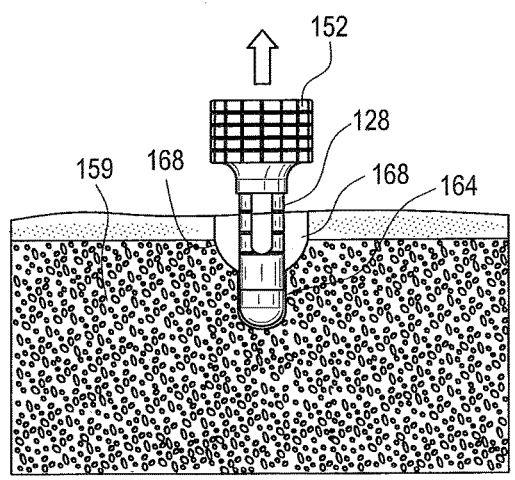

Continuing further, the cylindrical rotary cutter guide 128 is therefore now ready to receive the rotary cutter 136. Accordingly, as illustrated within FIG. 10, the rotary cutter 136 is moved downwardly so as to be operatively engaged within the cylindrical rotary cutter guide 128, it being noted that the support post or axle 140, not seen in FIG. 10, and the stub portion 144 of the support post or axle 140, are moved toward and inserted into the first vertically and diametrically extending through-slot 130 while the rotary cutting disk 138 will be moved toward and inserted into the second vertically and diametrically extending through-slot 132. As can then be seen in FIG. 11, when the support post or axle 144, not seen, and the stub portion 144 of the support post or axle 140 have effectively been inserted into the first vertically and diametrically extending through-slot 130 such that the support post or axle 144, not seen, and the stub portion 144 of the support post or axle 140 have encountered the bottom-most portion or lower terminal end portions of the first vertically and diametrically extending through-slot 130, the rotary cutting disk 138 will have formed slots 168,168 into portions of the patient's bone 159 which are located upon opposite sides of the drilled bore 164 and which effectively extend radially outwardly from the opposite sides of the drilled bore 164, as can best be seen in FIG. 12. Accordingly, the rotary cutter 136 is now moved upwardly so as to be withdrawn from the cylindrical rotary cutter guide 128 whereby only the cylindrical rotary cutter guide 128 remains at this point in time within the drilled bore 164. Subsequently, once again, the handle or handpiece 152 is fixedly secured to the upper end portion of the cylindrical rotary cutter guide 128, as seen in FIG. 13, and the assembly, comprising the handle or handpiece 152 and the cylindrical rotary cutter guide 128, is removed from the blind bore 164, as is illustrated within FIG. 14, leaving behind the blind bore 164 with its two oppositely disposed radially outwardly formed slots 168,168. The implant site is now ready to receive the single winged implant, as illustrated within FIGS. 1 and 2, and thus, a single winged implant 100 is in fact inserted into the blind bore 164, as disclosed within FIG. 15, wherein the oppositely disposed wing members 104 of the implant 100 will be readily accommodated within the two oppositely disposed radially outwardly formed slots 168,168. At this point in time, and as is well known in the art, an abutment, not shown, is attached to the upper end portion of the implant 100 so as to subsequently support a dental crown, also not shown, which completes the installation of the implant within the patient's jaw. As is illustrated within FIG. 16, bone allograft may then be deposited atop the implant 100 and the wing members 104,104 of the implant 100, by means of a suitable applicator 170, so as to effectively fill in the space or gap which exists above the implant 100 and the wing members 104,104 up to the top or crest portion of the jaw bone at the implant site. Allograft is well known in the art for facilitating and promoting osseoinegraton. Lastly, as illustrated within FIG. 17, the gum region 172 is sutured so as to effectively return the same to its original state.

In a similar manner, when it is desired to insert a dual winged implant into a patient's jaw, a dual implant rotary cutter guide assembly is utilized. More particularly, as can best be seen and appreciated from FIG. 18, the dual winged implant is generally indicated by the reference character 200 and is seen to effectively comprise two single implants, similar to the single implant 100 illustrated in FIGS. 1 and 2, however, in addition to the utilization of two single implants 100, 100, the single implants 100 are effectively connected together by means of an intermediary connecting bar or plate 230. It is to be noted that components parts of the dual winged implant 200 which correspond to component parts of the single winged implant 100 will be designated by corresponding reference characters except that they will be in the 200 series, although for brevity purposes, such corresponding components parts will not be discussed in detail. To the contrary, the description of the dual winged implant 200 will focus upon the differences between the single winged implant 100 and the dual winged implant 200. For example, it is to be noted that the wing members 204,204 are only provided upon the laterally external side wall portions of each implant body 202 while the oppositely disposed internal portions of each implant body portion 202 are integrally connected to the intermediary connecting bar or plate 230. In addition, or more particularly, it is also noted that the wing members 204,204 extend radially outwardly from their respective implant body portions 202 in diametrically opposite directions. The connecting bar or plate has a linear edge portion 232 extending along one of its upper or lower edge portions, depending upon whether or not the dual implant 200 is to be used within the maxillary or upper jaw bone 10, or within the mandible or lower jaw bone 12, and the linear edge portion 232 includes a longitudinally extending groove 234 defined therein. The opposite edge portion 236 of the connecting plate or bar 230 is radiused, and the oppositely disposed surface portions 238 of the connecting bar or plate 230 have a plurality of recesses 240 formed therein, all of these features being provided so as to promote osseointegration as has been discussed hereinbefore in connection with the first embodiment single implant 100. It is to be noted that similar to the longitudinal groove 234 defined within the linear edge portion 232, the radiused edge portion 236 can likewise be provided with a groove, not shown, and still further, the underside radiused portions of the wing members 204,204 can also be provided with similar grooves, not shown.

Having described the dual winged implant 200, a method for installing the dual winged implant 200 within a patient's jaw will now be described with reference to FIG. 19. FIG. 19 illustrates a dual implant rotary cutter guide assembly, generally indicated by the reference character 242, which is seen to comprise a transversely oriented rotary cutting disk guide 244 which comprises a central portion which is defined by means of two parallel plates 246,248 that are spaced apart from each other a sufficient distance so as to define a transversely extending slot 250 which is slightly larger than the thickness dimension of a planar rotary cutting disk, which is similar to the planar rotary cutting disk 138 illustrated within FIG. 4, whereby the planar rotary cutting disk can in fact be accommodated within the transversely oriented slot 250 defined between the two parallel plates 246,248 of the transversely oriented rotary cutting disk guide 244. Opposite ends of the two spaced parallel plates 246,248 are effectively joined together so as to form two annular ring members 252,254 which are integrally connected to the two spaced parallel plates 246,248. The two annular ring members 252,254 have diametrical extents that are sufficient to accommodate the upper end portions of a pair of cylindrical rotary cutter guides, of the type used in connection with the installation of a single winged implant, as illustrated at 128 within FIG. 3, when the two annular ring members 252,254 are effectively disposed over upper end portions of the pair of cylindrical rotary cutter guides 128,128 whereby the two annular ring members 252,254 will respectively surround each one of the pair of cylindrical rotary cutter guides 128,128.

Still further, it is to be noted that when the pair of cylindrical rotary cutter guides 128,128 are utilized in conjunction with the dual implant rotary cutter guide assembly 242, the second vertically and diametrically extending through-slots 132,132 defined within each one of the pair of cylindrical rotary cutter guides 128, 128 are disposed such that the second vertically and diametrically extending through-slots 132,132 of the pair of cylindrical rotary cutter guides 128,128 are disposed within the same plane as the transversely oriented slot 250 defined between the pair of transversely oriented parallel plates 246,248 of the transversely oriented rotary cutting disk guide 244. In this manner, when the rotary cutting disk, such as, for example, a rotary cutting disk similar to rotary cutting disk 138 illustrated within FIG. 3, is inserted into the transversely oriented slot 250 defined within the transversely oriented rotary cutting disk guide 244, oppositely disposed circumferential or peripheral side cutting portions of the rotary cutting disk can be accommodated within the second vertically and diametrically extending through-slots 132, 132 defined within the pair of cylindrical rotary cutter guides 128,128. Accordingly, the rotary cutting disk can then be utilized to form the radiused slot within the patient's jawbone for accommodating the connecting bar or plate 236 of the dual implant 200. As was the case with each one of the cylindrical rotary cutter guides 128, 128, each one of the pair of transversely oriented parallel plates 246,248 of the transversely oriented rotary cutting disk guide 244 is provided with a slot or notch 256,258 within the central upper edge portion of each plate 246,248. The slots or notches 256,258 are coaxially aligned with respect to each other for accommodating the support post or axle 140 of the rotary cutting disk 138 as well as the stub 144 portion of the support post or axle 138 so as to predetermine or precisely limit the extent to which the rotary cutting disk 138 can be moved downwardly relative to the transversely oriented rotary cutting disk guide 244, the pair of cylindrical rotary cutter guides 128,128, and the patient's jawbone. In this manner, the depth of the radiused slot, defined within the patient's jawbone for accommodating the transversely oriented connecting plate or bar 236 of the dual dental implant 200, is precisely defined and predetermined.

To conclude this disclosure, a method of implanting the dual implant 200, as disclosed within FIG. 18, will now be discussed. In accordance with this method, the dental technician or dentist will of course select the site at which the two dental implants will in fact be implanted. At each implantation site, the dental technician or dentist will perform the method steps as previously described in connection with FIGS. 6-12, that is, briefly, the blind bore 164 is drilled, the cylindrical rotary cutter guide 128 is inserted into the blind bore 164, the rotary cutter 136 is engaged with the cylindrical rotary cutter guide 128, the rotary cutter 136 is utilized to form the oppositely disposed slots for accommodating the oppositely disposed winged members 104,104 of the single implant, the rotary cutter 136 is removed from the cylindrical rotary cutter guide 128, but the cylindrical rotary cutter guide 128 is not removed from each dental implant site but is permitted to remain disposed within each one of the blind bores 164,164 formed within the patient's jaw. Therefore, two cylindrical rotary cutter guides 128,128 now project outwardly from their respective blind bores 164,164, and at this point in time, the dual implant rotary cutter guide assembly 242 is moved over the two outwardly projecting cylindrical rotary cutter guides 128,128 such that the two oppositely disposed annular ring members 252,254 of the dual implant rotary cutter guide assembly 242 respectively surround the outwardly projecting cylindrical rotary cutter guides 128, 128. A rotary cutting disk, similar to the rotary cutting disk 138 of the rotary cutter 136 illustrated within FIG. 4 but which may be different in size so as to provide a radiused slot sufficient in size to accommodate the transversely oriented connecting bar or plate 230 of the dual implant 200 as well as the radiused edge portion 236 of the connecting bar or plate 230 of the dual implant 200, is then inserted into the transversely oriented slot 250 of the dual implant rotary cutter guide assembly 242 while the oppositely disposed peripheral edge portions of such rotary cutting disk 138 are accommodated within the second vertically and diametrically extending through-slots 132 of the cylindrical rotary cutter guides 128,128.

In addition, the support post 140 and stub portion 144 of the rotary cutter 136 are respectively disposed within the notches or slots 256,258 formed within the oppositely disposed plates 246,248 of the dual implant rotary cutter guide assembly 242 so as to again precisely limit the depth to which the rotary cutting disk 138 will form the transversely oriented slot for accommodating the transversely oriented connecting bar or plate 230 of the dual implant 200 as well as the radiused edge portion 236 of the connecting bar or plate 230. Accordingly, the rotary cutting disk 138 can then be actuated so as to in fact cut the radiused slot for accommodating the connecting bar or plate 230 of the dual implant 200 as well as the radiused edge portion 236 of the connecting bar or plate 230. It is to be noted that as a result of the cutting operation performed by means of the rotary cutting disk 138 utilized for forming the radiused slot for accommodating the connecting bar or plate 230 and the radiused edge portion 236 of the connecting bar or plate 230, the laterally internal radiused slots 168,168, previously formed in connection with the radiused slots for accommodating the winged members 104,104 of the single implants 100,100, will have effectively been reshaped or re-cut such that only the oppositely disposed external radiused slots 168,168, previously formed in connection with the radiused slots for the winged members 104,104 of the single implants 100, 100, remain so as to accommodate the oppositely disposed external winged members 204,204 of the dual implant 200. Subsequent to these operations, the rotary cutter 136 is withdrawn or retracted from the dual implant rotary cutter guide assembly 242, in a manner similar to that shown in FIG. 12, the dual implant rotary cutter guide assembly 242 is removed from its disposition around the single implant cylindrical rotary cutter guides 128,128, the cylindrical rotary cutter guides 128,128 are removed from the two implant sites in a manner similar to that shown in FIGS. 13 and 14, the dual implant 200 is then inserted into the patient's jaw in a manner similar to that illustrated within FIG. 15, bone allograft is then deposited over the dual implant 200 in a manner similar to that illustrated within FIG. 16, and the patient's gum is sutured in a manner illustrated within FIG. 17.

Obviously, many variations and modifications of the present invention are possible in light of the above teachings. It is therefore to be understood that within the scope of the appended claims, the present invention may be practiced otherwise than as specifically described herein.

KEY TO REFERENCE NUMBERS

100—Single implant with opposite wing members
102—Body portion of implant 100
104—Wing members on implant 100
106—Vertically oriented leg of right triangle configured wing member 104
108—Horizontally oriented leg of right triangle configured wing member 104
110—Longitudinal axis of implant body portion 102
112—Hypotenuse side of right triangle configured wing member 104
114—Linear groove in upper edge portion of 108
118—Recesses in side surface portions 120 of wing members 104
120—Side surface portions of wing members 104
122—Ring members/cavities in central, lower external portions of 102
124—Ring members/cavities in upper external portions of 102
126—Elliptical recesses in body portion 102 of implant 100
128—Rotary cutting guide
130—First vertically extending through-slot of 128
132—Second vertically extending through-slot
134—Upstanding leg portions of 128
136—Rotary cutter
138—Rotary cutting disk of 136
140—Support post or axle of 136
142—Longitudinal axis of 136
144—Stub portion of 140
146—Outer peripheral cutting teeth of 138
148A—Holes or apertures in cutting disk 138A
150A—Radial slots in cutting disk 138A
152—Handpiece for grasping 128
154—Upper cylindrical housing or handle of 152
156—Lower cylindrical connector portion of 152
158—Male connector of 152
159—Bone region of jaw within which an implantation site is to be formed
160A-160E—Drill bits of progressively larger diametrical extents
162—Depth markings on drill bits 160A-160E
164—Blind bore formed at implantation site
168—Radiused slots formed in bone for accommodating implant wings 104
170—Applicator for applying allograft atop winged implant 100
172—Sutured gum line of patient
200—Second embodiment dual winged implant
202—Implant body portion
204—Wing member
230—Connecting bar or plate of 200
232—Linear edge portion of 230
234—Linear groove within linear edge portion 232
236—Radiused edge portion of 230
238—Opposite surface portions of 230
240—Recesses within surface portions 238
242—Dual implant rotary cutter guide assembly
244—Transversely extending central portion of 242
246—First plate member of 244
248—Second plate member of 244

250—Central slot within 244
252, 254—Annular ring members for accommodating the pair of guides 128
256,258—Notches within plates 246,248

What is claimed as new and desired to be protected by Letters Patent of the United States of America, is:

1. A system for implementing the installation of a winged dental implant within a blind bore implantation site defined within a patient's jaw, comprising:
    a rotary cutter assembly comprising a rotary cutting disk mounted upon a support post; and
    a rotary cutter guide to be disposed within the blind bore implantation site defined within the patient's jaw, wherein said rotary cutter guide comprises a base portion and an upstanding body portion, a first vertically extending through-slot defined within said upstanding body portion of said rotary cutter guide such that said first vertically extending through-slot extends through said rotary cutter guide along a first plane from a first wall portion of said upstanding body portion to a second oppositely disposed wall portion of said upstanding body portion, and a second vertically extending through-slot defined within said rotary cutter guide such that said second vertically extending through-slot extends through said rotary cutter guide along a second plane which is disposed orthogonally with respect to said first plane such that said second slot extends from a third wall portion of said upstanding body portion to a fourth oppositely disposed wall portion of said upstanding body portion,
    wherein said support post of said rotary cutter assembly extends through said first vertically extending through-slot defined within said upstanding body portion of said rotary cutter guider while oppositely disposed stub portions of said support post extend outwardly from said oppositely disposed first and second wall portions of said first vertically extending through-slot defined within said upstanding body portion of said rotary cutter guide so as to stably support said rotary cutter assembly within said rotary cutter guide, and opposite sides of said rotary cutting disk project outwardly from said oppositely disposed third and fourth wall portions of said second vertically extending through-slot defined within said upstanding body portion of said rotary cutter guide so as to be capable of cutting oppositely disposed slots within the patient's jaw for accommodating oppositely disposed wing members of the winged dental implant.

2. The system as set forth in claim 1, wherein:
    said first vertically extending through-slot, and said second vertically extending through-slot oriented orthogonally with respect to said first vertically extending through-slot, separate an upper portion of said rotary cutter guide into four upstanding leg sections.

3. The system as set forth in claim 1, wherein:
    said first vertically extending through-slot has a first predetermined vertical depth as defined within said rotary cutter guide,
    and said second vertically extending through-slot has a second predetermined vertical depth as defined within said rotary cutter guide.

4. The system as set forth in claim 3, wherein:
    said first predetermined vertical depth of said first vertically extending through-slot defined within said rotary cutter guide is less than said second predetermined vertical depth of said second vertically extending through-slot defined within said rotary cutter guide such that a longitudinal axis of said rotary cutter assembly is disposed at a predetermined elevational level above a bottom portion of the blind bore implantation site while opposite side portions of said rotary cutting disk project outwardly from opposite side portions of said rotary cutter guide in order to cut slots within the patient's jaw at vertical elevational levels which extend beneath the elevational level at which said longitudinal axis of said rotary cutter assembly is disposed.

5. The system as set forth in claim 1, further comprising:
    a handpiece for grasping said rotary cutter guide in order to facilitate installation and removal of said rotary cutter guide into and out from the blind bore implantation site.

6. The system as set forth in claim 5, wherein:
    said handpiece is provided with a male connector which has the configuration of a cruciform comprising a first cross-piece having a first predetermined width dimension for permitting said first cross-piece of said cruciform to be accommodated within said first vertically extending through-slot defined within said rotary cutter guide, and a second cross-piece having a second predetermined width dimension for permitting said second cross-piece of said cruciform to be accommodated within said second vertically extending through slot defined within said rotary cutter guide.

7. The system as set forth in claim 1, wherein said system comprises:
    a dual implant rotary cutter guide assembly for implementing the installation of a dual winged dental implant within a pair of blind bore implantation sites defined within a patient's jaw.

8. The system as set forth in claim 7, wherein:
    said dual implant rotary cutter guide comprises a pair of rotary cutter guides which are respectively to be disposed within said pair of blind bores defined within said blind bore implantation sites.

9. The system as set forth in claim 8, wherein said dual implant rotary cutter guide assembly comprises:
    a central, transversely oriented slotted section disposed within a first plane for accommodating said rotary cutter disk;
    a pair of annular ring members disposed upon opposite sides of said transversely oriented slotted section for annularly surrounding said pair of rotary cutter guides when said dual implant rotary cutter guide is disposed over said pair of rotary cutter guides; and
    a notch defined within an upper edge portion of said central, transversely oriented slotted section and extending within a second plane, orthogonal to said first plane, for accommodating said support post and said stub portions of said rotary cutter.

10. The system as set forth in claim 9, wherein:
    said central, transversely oriented slotted section comprises a pair of transversely extending plate members spaced from each other so as to define a transversely oriented slot therebetween wherein said slot extends along said first plane.

11. The system as set forth in claim 10, wherein:
    a notch is defined within an upper edge portion of each one of said pair of transversely extending plate members, wherein said notches are coaxially aligned with respect to each other so as to accommodate said support post and said stub portions of said rotary cutter support post.

12. A method for installing a single winged dental implant, having wing members extending radially outwardly from opposite sides of a body portion of said single winged dental implant, into a patient's jaw, comprising the steps of:
- drilling a blind bore within the patient's jaw at a predetermined dental implant implantation site;
- inserting a cylindrical rotary cutter guide within said drilled blind bore, wherein said cylindrical rotary cutter guide comprises a base portion and an upstanding body port which has a first vertically extending through-slot defined within said upstanding body portion of said cylindrical rotary cutter guide such that said first vertically extending through-slot extends through said cylindrical rotary cutter guide along a first diametrical plane, and a second vertically extending through-slot defined within said upstanding body portion of said cylindrical rotary cutter guide such that said second vertically extending through-slot extends through said upstanding body portion of said cylindrical rotary cutter guide along a second diametrical plane which is disposed orthogonally with respect to said first diametrical plane;
- inserting a rotary cutter assembly, comprising a rotary cutting disk mounted upon a support post, into said cylindrical rotary cutter guide such that said support post of said rotary cutter assembly extends through said first vertically extending through-slot of said cylindrical rotary cutter guide and stub portions of said support post extend outwardly from opposite ends of said first vertically extending through-slot defined within said cylindrical rotary cutter guide and from oppositely disposed first and second side wall portions of said upstanding body portion of said cylindrical rotary cutter guide so as to stably support said rotary cutter assembly within said cylindrical rotary cutter guide, while opposite sides of said rotary cutting disk project outwardly from opposite ends of said second vertically extending through-slot defined within said cylindrical rotary cutter guide and from oppositely disposed third and fourth wall portions of said upstanding body portion of said cylindrical rotary cutter guide so as to be capable of cutting oppositely disposed slots within the patient's jaw for accommodating said oppositely disposed wing members of the single winged dental implant;
- removing said rotary cutter assembly from said cylindrical rotary cutter guide and removing said cylindrical rotary cutter guide from said drilled blind bore; and
- inserting said single winged dental implant into said drilled blind bore such that said body portion of said single winged implant is disposed within said drilled blind bore while said oppositely disposed wing members of said single winged implant are disposed within oppositely disposed radiused slots formed by said opposite sides of said rotary cutting disk.

13. The method as set forth in claim 12, further comprising the step of:
- inserting allograft atop said single winged implant, implanted within said drilled blind bore, so as to promote osseointegration.

14. The method as set forth in claim 13, further comprising the step of:
- suturing the implantation site so as to return said implantation site to its original state.

15. A method for installing a dual winged dental implant, comprising a pair of single winged implant body portions connected together by a connecting plate or bar and having wing members extending radially outwardly from opposite sides of said dual winged dental implant, into a patient's jaw, comprising the steps of:
- drilling a blind bore within the patient's jaw at two predetermined dental implant implantation sites;
- inserting a cylindrical rotary cutter guide within each one of said two drilled blind bores, wherein each one of said cylindrical rotary cutter guides comprises a base portion and an upstanding body portion which has a first vertically extending through-slot defined within said upstanding body portion of said cylindrical rotary cutter guide such that said first vertically extending through-slot extends through said cylindrical rotary cutter guide along a first diametrical plane, and a second vertically extending through-slot defined within said upstanding body portion of said cylindrical rotary cutter guide such that said second vertically extending through-slot extends through said upstanding body portion of said cylindrical rotary cutter guide along a second diametrical plane which is disposed orthogonally with respect to said first diametrical plane;
- mounting a dual implant rotary cutter guide assembly, comprising a central, transversely oriented slotted section, coplanar with said pair of first through-slots defined within said pair of rotary cutter guides, for accommodating said rotary cutting disk, a notch defined within an upper edge portion of said central, transversely oriented slotted section and extending within a second plane, orthogonal to said first plane, and a pair of annular ring members disposed upon opposite ends of said transversely oriented slotted section, over said pair of cylindrical rotary cutter guides such that said pair of annular ring members annularly surround said pair of cylindrical rotary cutter guides;
- mounting a rotary cutter assembly, comprising a rotary cutting disk mounted upon a support post, upon said dual implant rotary cutter guide such that said support post of said rotary cutter assembly is disposed within said transversely oriented slotted section of said dual implant rotary cutter guide while said stub portions of said support post are supported within said notch of said central, transversely oriented slotted section of said dual implant rotary cutter guide, whereby said rotary cutting disk can form a first radiused slot within the patient's bone for accommodating said connecting bar or plate of said dual winged dental implant while opposite sides of said rotary cutting disk pass through said second slots defined within said pair of cylindrical rotary cutter guides so as to form second radiused slots within the patient's bone for accommodating oppositely disposed wing members of said dual winged implant;
- removing said rotary cutter assembly from said dual implant rotary cutter guide;
- removing said dual implant rotary cutter guide from said implantation site;
- removing each one of said cylindrical rotary cutter guides from each one of said drilled blind bores; and
- inserting said dual winged dental implant into said implantation site such that said body portions of said pair of single winged implants are disposed within said drilled blind bores while said connecting bar or plate is disposed within said first radiused slot and said oppositely disposed wing members of said dual winged implant are disposed within said oppositely disposed second radiused slots.

16. The method as set forth in claim 15, further comprising the step of:

inserting allograft atop each one of said winged implants, implanted within said drilled blind bores, so as to promote osseointegration.

17. The method as set forth in claim 16, further comprising the step of:

suturing the implantation site so as to return said implantation site to its original state.

\* \* \* \* \*